United States Patent [19]

Tepic

[11] Patent Number: 5,246,461
[45] Date of Patent: Sep. 21, 1993

[54] FEMORAL TWIN-SET FOR A HIP ENDOPROSTHESIS

[75] Inventor: Slobodan Tepic, Davos, Switzerland

[73] Assignee: Laboratorium für experimentelle Chirurgie, Forschungsinstitut, Davos, Davos, Switzerland

[21] Appl. No.: 618,662

[22] Filed: Nov. 27, 1990

[51] Int. Cl.$^5$ .............................................. A61F 2/32
[52] U.S. Cl. .......................................... 623/23; 623/18
[58] Field of Search ...................... 623/23, 16, 18, 19, 623/20

[56] References Cited

U.S. PATENT DOCUMENTS

| | | | |
|---|---|---|---|
| 3,320,951 | 5/1967 | Wittebol | 623/23 |
| 4,064,567 | 12/1977 | Burstein et al. | 623/23 |
| 4,199,824 | 4/1980 | Niederer | 623/23 |
| 4,516,277 | 5/1985 | Butel | 623/23 |
| 4,756,711 | 7/1988 | Maï | 623/23 |

FOREIGN PATENT DOCUMENTS

0390768 10/1990 European Pat. Off. .............. 623/23

*Primary Examiner*—David Isabella
*Attorney, Agent, or Firm*—McAulay Fisher Nissen Goldberg & Kiel

[57] ABSTRACT

This invention describes a femoral twin-stem for a hip endoprosthesis. The lateral stem portion and the medial stem portion are connected by a bridge. The neck of the femoral twin-stem is connected to the proximal section of the lateral stem portion. The proximal prong of the medial stem portion and the distal prong of the lateral stem portion allow for a gradual load transfer to the bone since they can be individually designed with a proper geometry all the way to their respective tips. Gradual load transfer in turn reduces stresses in the bone cement mantle and improves the long term results of the hip replacement effected with this femoral twin-stem.

19 Claims, 6 Drawing Sheets

FEMORAL TWIN-SET FOR A HIP ENDOPROSTHESIS

FIELD OF THE INVENTION

This invention relates to femoral twin-stem for a hip endoprosthesis.

BACKGROUND OF THE INVENTION

Replacement surgery for artificial joints, in particular of the femoral component of hip joints, entails removal of the bone end-section. The end of the bone and the corresponding joint component are replaced with a prosthesis which must assume the load supporting function. Joint forces are transferred from the prosthesis to the bone. From the very early days of joint replacement till today the preferred mode for anchoring the prosthetic component in the tubular bone has been by means of a stem, i.e. a rod-shaped extension of the prosthesis properly adapted to the shape and size of the medullary cavity. Since the early sixties the standard procedure has included the use of so-called bone cement. Bone cement is a room temperature curing acrylate (usually in the form of a powder component consisting of polymethylmethacrylate with a catalyst and a liquid component consisting of methylmethacrylate with an accelerator, the two components polymerizing upon mixing with each other) with additives such as zirconium oxide (for obtaining radiographic density) and antibiotics. When cured, bone cement forms a relatively soft (about five to ten times softer than cortical bone) mantle between the prosthesis stem and the bone. Stresses induced in this cement mantle by load transfer from the stem to the bone depend on the compliances of the stem and of the bone.

In general, a stiffer stem will transfer loads closer to its tip, i.e. more distally in the case of the femoral component of the hip joint; a more compliant stem will transfer loads closer to the neck, i.e. more proximally. Gradual change of the stem cross-section (smaller cross-section distally) results in more gradual load transfer. This works well for the distal part of the stem, but it moves the load transfer more proximally, where the cross-section of the stem cannot be sufficiently reduced since it must support the joint loads transferred to it via the neck of the prosthesis. In addition, the bone tube is opened at this side and thus rendered even softer. To achieve a truly uniform load transfer the stem should reduce its stiffness all the way to zero at its proximal end.

SUMMARY OF THE INVENTION

The invention as claimed is intended to remedy these drawbacks. It solves the problem of how to design a femoral twin-stem for a hip endoprosthesis which allows for a truly uniform load transfer.

The joint load on the hip joint prosthesis produces a bending moment on the stem which in turn generates compressive stresses on the medial proximal and the lateral distal aspect of the cement mantle. This is where most of the load transfer occurs. Lateral proximal aspect of the femur is the area of soft cancellous bone and does not support much load. Thus the neck of the prosthesis is connected to the proximal aspect of the lateral stem where there is very little load transfer between the prosthesis and the bone. High stiffness of the stem in this region does not induce high stress concentration in the cement. Two stem portions are connected at their midsection. From there the medial stem portion gradually reduces its stiffness in both the proximal and the distal directions. Proximal direction is more important for the overall load transfer. The lateral stem portion also reduces its stiffness in the distal direction.

With this configuration a truly uniform load transfer can be achieved in the frontal plane where the highest joint loads occur. Gradual load transfer reduces peak loads in the cement mantle. As it is well known, bone cement is the weakest and thus the most critical component of the total joint replacement. Reducing the stresses in the bone cement thus improves long term results of this very important surgical treatment of the joint diseases.

The various features of novelty which characterize the invention are pointed out with particularity in the claims annexed to and forming part of this disclosure. For the better understanding of the invention, its operating advantages and specific objects attained by its use, reference should be had to the accompanying drawings and descriptive matter in which are illustrated and described preferred embodiments of the invention.

DESCRIPTION OF THE PREFERRED EMBODIMENTS

Figure 1:
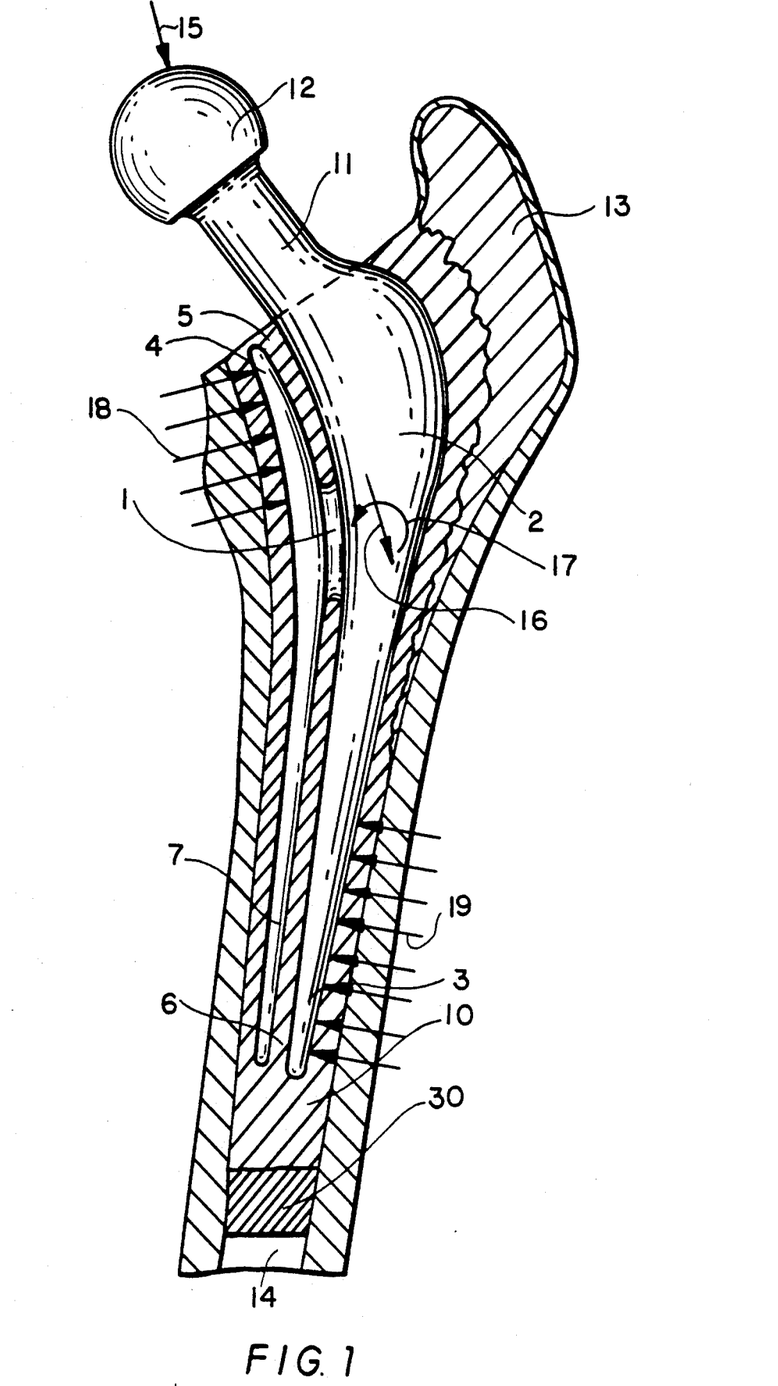
FIG. 1 is a sectional view of the femoral twin-stem according to the invention cemented in the proximal part of the femur.

FIG. 1 represents the femoral twin-stem according to the invention inserted in the proximal femur. The lateral stem proximal section 2 is shaped much as a conventional stem proximal section with the neck of the prosthesis 11 supporting the head of the prosthesis 12. The neck of the prosthesis 11 is located between the head of the prosthesis 12 and the lateral stem proximal section 2 and which is in general correspondence with the neck of the natural femur. Total twin-stem height is measured therefore from the neck 11 to lateral stem proximal section 2 transition to the tip of the latter. Antero-posterior cuts 5 and 6 separate the lateral stem portion 2,3 from the medial stem portion 4,7. Stiffness of the distal prong 3 of the lateral stem portion 2,3 reduces in distal direction to facilitate uniform load transfer to the bone through the cement mantle 10. Medial stem portion 4,7 is connected to the lateral stem portion 2,3 by bridge 1 located in the central region of the stem. Both the distal prong 7 and proximal prong 4 of the medial stem portion 4,7 have a reduced stiffness towards their respective tips. The lateral proximal aspect 13 of the femur 14 is made of soft cancellous bone and does not support much of the joint force 15. Thus the proximal section 2 of the lateral stem portion 2,3 serves basically as a neck extension, transferring the joint load 15 down to the bridge 1 level of the twin-stem. At this level the joint force 15 reduces to the force 16 (equal to the joint force 15 in magnitude and direction) and the moment 17. The moment 17 is balanced mostly by compressive stresses 18 on the proximal prong 4 of the medial stem portion 4,7 and compressive stresses 19 on the distal prong 2 of the lateral stem portion 2,3. The force 16 is balanced by shear and compressive forces in the cement mantle 10, which are generally of lower magnitude and less concern.

Figure 2:
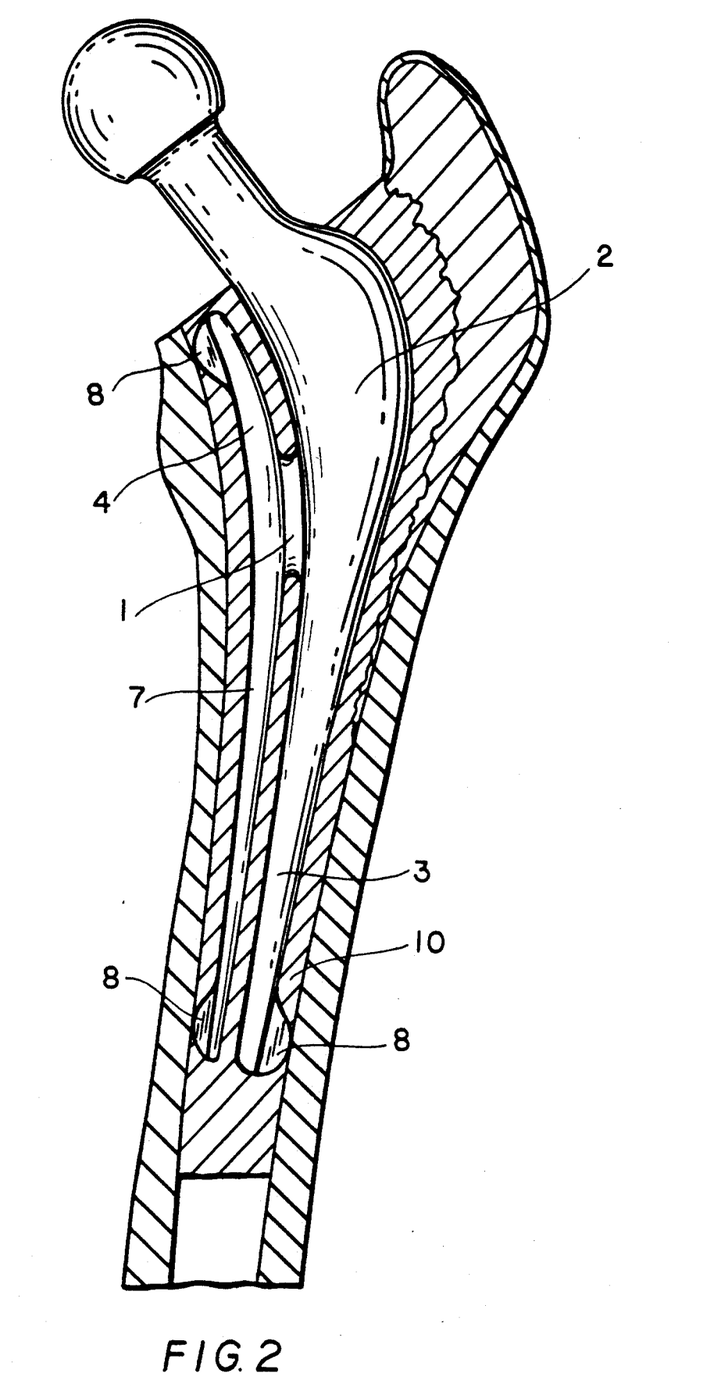
FIG. 2 is a sectional view of a preferred embodiment of the invention according to FIG. 1.

As shown in FIG. 2, to maintain a minimum thickness of the cement mantle 10, especially at the lateral distal and medial proximal aspects, the respective tips may be shaped so as to form thin protrusions 8.

Figure 3:
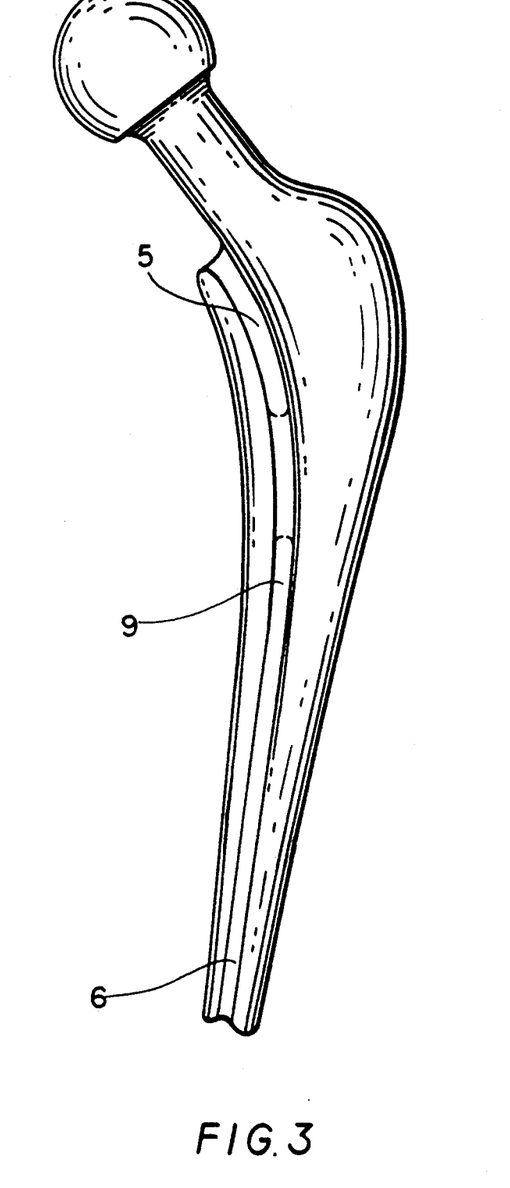
FIG. 3 is a side view of a preferred embodiment of the invention in which the cuts are filled with a polymer.

FIG. 3 shows a preferred embodiment of the invention in which the antero-posterior cuts 5 and 6 are filled with a polymer 9, preferably polymethylmethacrylate (PMMA) and/or polybutylmethacrylate (PBMA).

Figure 4A:
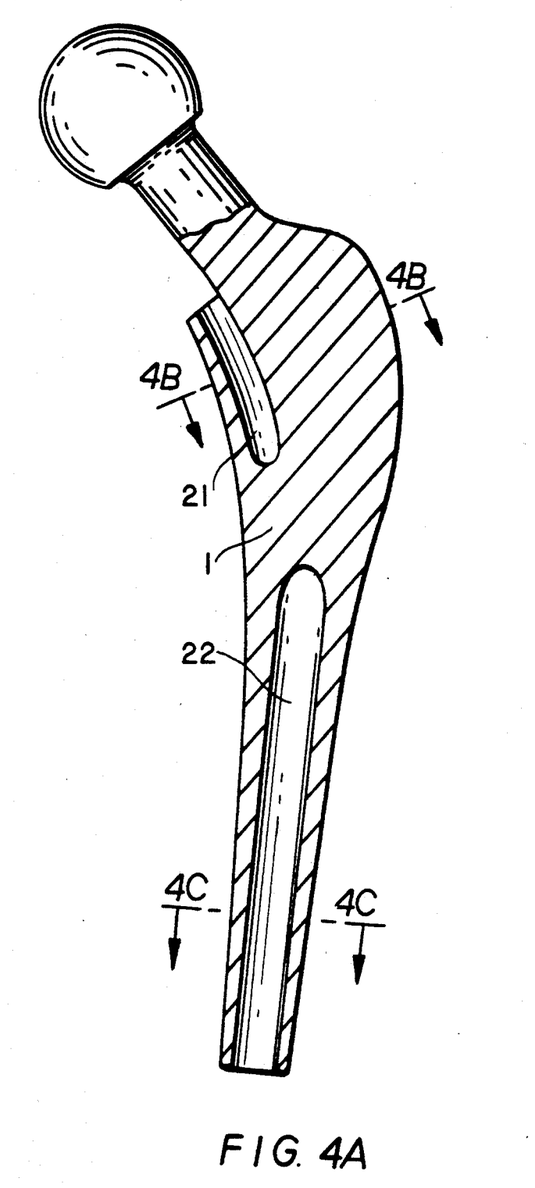
FIG. 4 is a sectional view of another preferred embodiment of the invention with a distal tubular structure.
Figure 4B:
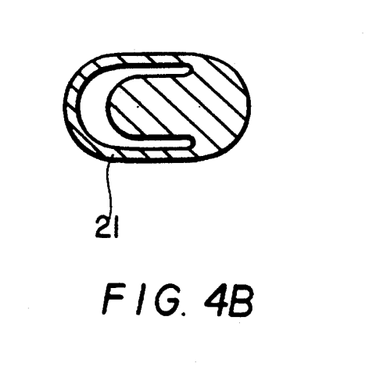
Figure 4C:
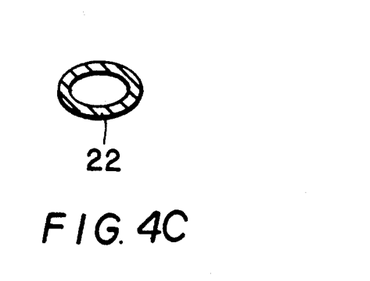
Figure 5A:
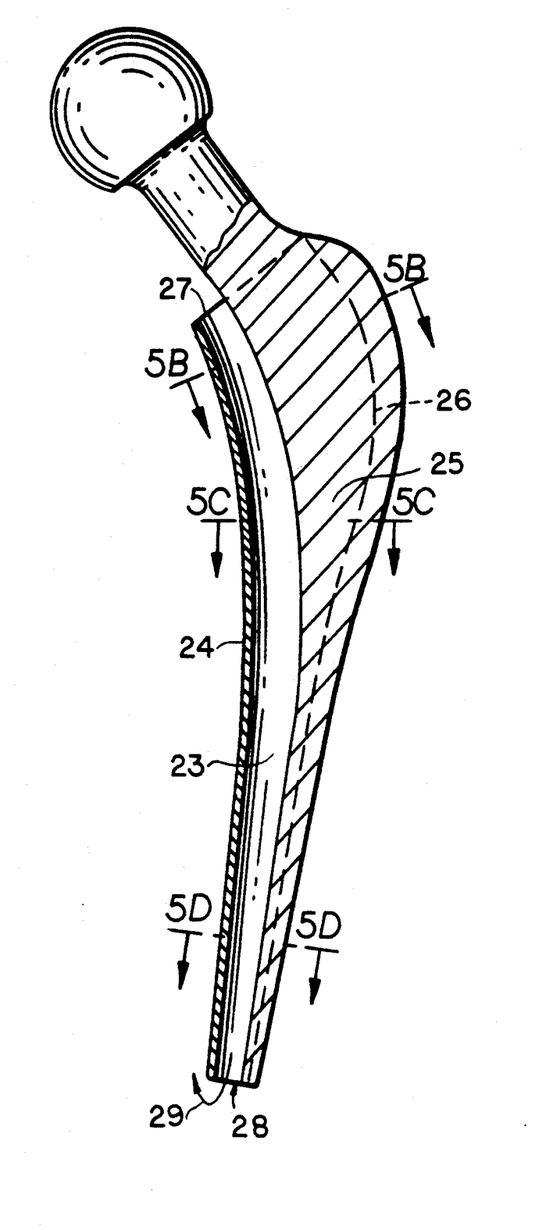
FIG. 5 is a sectional view of a modification of the embodiment according to FIG. 4 with a single tubular structure.
Figure 5B:
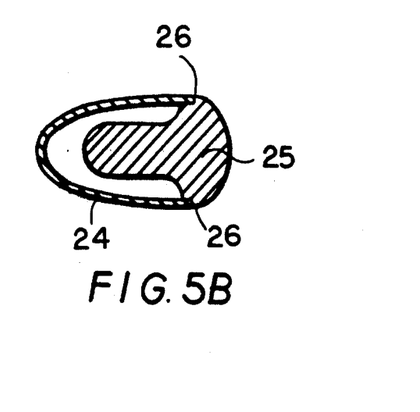
Figure 5C:
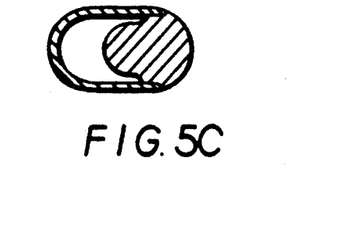
Figure 5D:
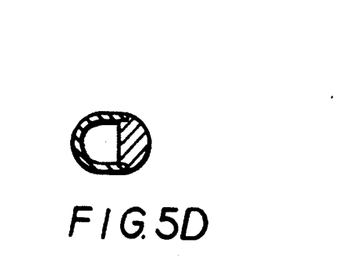

FIG. 4 shows another preferred embodiment of the invention in which two distal prongs 3 and 7 are connected in the antero-posterior region of the twin-stem to form a lower tubular structure 22, extending distally from the bridge 1. This lower tubular structure (as seen in the section A—A) is preferably designed with gradually reducing stiffness towards the distal end of the twin-stem thus reducing stresses 19 in the cement mantle 10.

The proximal section 2 of the lateral stem portion 2,3 and the proximal prong 4 of the medial stem portion 4,7 are connected in the antero-posterior region of the twin-stem to form an upper tubular structure 21, extending proximally from the bridge 1. The advantage of the relatively soft upper tubular structure 21 (as represented in section B—B) is the reduction of stresses 18 in the cement mantle 10.

FIG. 5 shows a modification of the preferred embodiment of a femoral twin-stem according to FIG. 4 in which bridge 1 is eliminated thereby connecting said lower and upper tubular structures 21;22 into a single tubular structure 23. Medial tubular stem portion 24 of the single tubular structure 23 is connected to the lateral tubular stem portion 25 of the single tubular structure 23 along the lines 26. The preferable method of joining the two portions 24 and 25 is by welding.

This construction allows for control of the stem compliance in both distal and proximal directions thus minimizing stresses in the cement mantle 10.

Alternatively the single tubular structure 23 can be used as an injection nozzle for the bone cement to be introduced in the medullary canal. To this purpose the proximal opening 27 of the single tubular structure 23 is provided with an adaptor to the caulking gun delivering the bone cement distally through the single tubular structure 23 and then after passing distal opening 28 retrogradly between the twin-stem and the bone as indicated by arrow 29. This procedure necessitates of course the use of a medullary plug 30 as shown in FIG. 1. The advantage of this procedure are the better quality of the cement mantle 10 as well as the convenience of the prosthesis placement prior to the cement injection.

Figure 6:
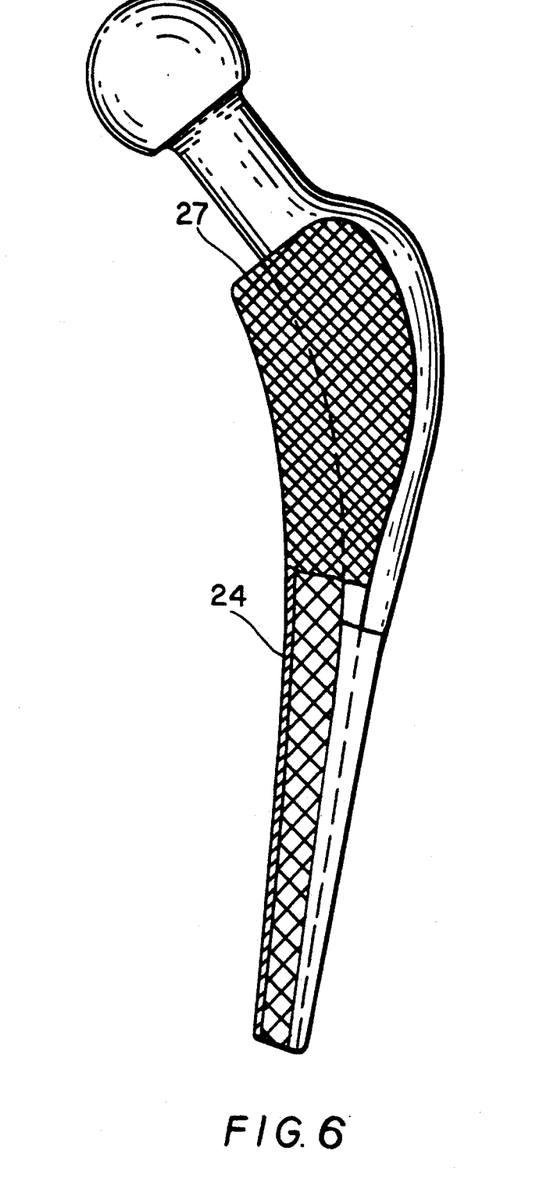
FIG. 6 is a side view of another preferred embodiment of the invention with a wire mesh tubular structure.

FIG. 6 shows still another preferred embodiment of the invention in which the medial tubular stem portion 24 of the single tubular structure 23 is formed by a wire mesh. Use of a wire mesh (instead of a thin shell as in the embodiment according to FIG. 5) allows for a further degree of compliance control. Space within the tubular structures 21, 22 or 23 of the twin-stems according to FIGS. 4 to 6 are preferably filled with a polymer, preferably polymethylmethacrylate (PMMA) and/or polybutylmethacrylate (PBMA).

While the foregoing description and drawings represent the preferred embodiments of the present invention, it will be obvious to those skilled in the art that various changes and modifications may be made therein without departing from the true spirit and scope of the present invention.

I claim:

1. Femoral twin-stem for a hip endoprosthesis, comprising a lateral stem portion and a medial stem portion, said lateral stem portion and said medial stem portion being connected by a bridge, said bridge being approximately centrally located along the length of said lateral stem portion, said bridge being constructed so that said lateral and medial stem portions are separated from each other by an antero-posterior proximal open slot and an antero-posterior distal open slot both extending away from said bridge.

2. Femoral twin-stem according to claim 1, wherein said medial stem portion is divided by said bridge into a proximal prong and a first distal prong and said lateral stem portion is divided by said bridge into a proximal section and a second distal prong, said endoprosthesis having a neck, said proximal section being connected to the neck of the endoprosthesis and said second distal prong having a distal end.

3. Femoral twin-stem according to claim 2 having a total twin-stem length, said total twin-stem length being measured from the transition between said neck and said lateral stem proximal section to said tip of said second distal prong.

4. Femoral twin-stem according to claim 3, wherein said proximal slot has a length of 1/5 to ½ of the total twin-stem length.

5. Femoral twin-stem according to claim 2, wherein said distal prong of said medial stem portion is shorter than the distal prong of said lateral stem portion (2,3).

6. Femoral twin-stem according to claim 3, wherein said distal slot has a length of 1/5 to 3/5 of the total twin-stem length.

7. Femoral twin-stem according to claim 2, wherein said distal prong of said lateral stem portion has a lateral protrusion, preferably at the distal end of said distal prong, acting as a bone cement spacer.

8. Femoral twin-stem according to claim 2, wherein said proximal and distal prongs of said medial stem portion have medial protrusions acting as bone cement spacers.

9. Femoral twin-stem according to claim 2, wherein said two distal prongs are connected in the antero-posterior region of said twin-stem to form a lower tubular structure extending distally from said bridge.

10. Femoral twin-stem according to claim 2, wherein said proximal prong and said proximal section are connected in the antero-posterior region of said twin-stem to form an upper tubular structure extending proximally from said bridge.

11. Femoral twin-stem according to claim 9, wherein the medial tubular stem portion of said single tubular structure is formed by a wire mesh.

12. Femoral twin-stem according to claim 1, wherein the space within the antero-posterior open slots are filled with a polymer, preferably polymethylmethacrylate (PMMA) or polybutylmethacrylate (PBMA).

13. Femoral twin-stem according to claim 2, wherein said bridge is located nearer a proximal portion of the femoral stem.

14. Femoral twin-stem for a hip endoprosthesis comprising a lateral stem portion and a medial stem portion, said lateral stem portion and said medial stem portion being connected by a bridge, said bridge being approximately centrally located along the length of said lateral stem portion, said bridge being constructed so that said lateral and medial stem portions are separated from each other by an antero-posterior proximal open slot and an antero-posterior distal open slot both extending away from said bridge, wherein said endoprosthesis has a neck, said lateral stem portion being divided by said bridge into a proximal section and a distal prong, said proximal section being connected to the end of the endoprosthesis and said distal prong has a distal end and wherein said medial stem portion extends only proximally into a proximal prong.

15. Femoral twin stem for a hip endoprosthesis comprising a lateral stem portion and a medial stem portion, said medial stem portion having a proximal prong and first distal prong, said lateral stem portion having a proximal section and a second distal prong, said two distal prongs being connected in the antero-posterior region of said twin stem to form a lower tubular structure, said proximal prong and said proximal section being connected in the antero-posterior region of said twin-stem to form an upper tubular structure, said lower and upper tubular structure being connected to form a single tubular structure. being connected in the antero-posterior region of said twin-stem to form an upper tubular structure, said lower and upper tubular structure being connected to form a single tubular structure.

16. Femoral twin stem according to claim 1 wherein the space within the antero-posterior open slots is filled with a polymer, preferably polymethylmethacrylate (PMMA).

17. Femoral twin stem according to claim 9 or claim 10 wherein the space within the tubular structure is filled with a polymer, preferably polymethylmethacrylate (PMMA).

18. Femoral twin stem according to claim 1 wherein the space with the antero-posterior open slots is filled with a polymer, preferably polybutylmethacrylate (PBMA).

19. Femoral twin stem according to claim 9 or claim 10 wherein the space within the tubular structure is filled with a polymer, preferably polybutylmethacrylate (PBMA).

* * * * *

UNITED STATES PATENT AND TRADEMARK OFFICE
CERTIFICATE OF CORRECTION

PATENT NO. : 5,246,461
DATED : September 21, 1993
INVENTOR(S) : Slobodan Tepic

It is certified that error appears in the above-identified patent and that said Letters Patent is hereby corrected as shown below:

Title page, item [54] and col. 1, lines 1-2, "FEMORAL TWIN-SET FOR A HIP ENDOPROSTHESIS" should read --FEMORAL TWIN-STEM FOR A HIP ENDOPROSTHESIS--

Signed and Sealed this

Twenty-second Day of March, 1994

Attest:

BRUCE LEHMAN

Attesting Officer

Commissioner of Patents and Trademarks